(12) United States Patent
Cumming

(10) Patent No.: US 6,503,275 B1
(45) Date of Patent: *Jan. 7, 2003

(54) OPHTHALMIC LENS INSERTION INSTRUMENT AND PACKAGE

(75) Inventor: J. Stuart Cumming, Anaheim, CA (US)

(73) Assignee: Medevec Licensing, B.V., Amsterdam (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/751,181

(22) Filed: Nov. 15, 1996

(51) Int. Cl.[7] .................................................. A61F 2/16
(52) U.S. Cl. ........................ 623/6.12; 623/6.43; 606/107
(58) Field of Search ..................... 623/4, 6, 4.1, 6.11, 623/6.12, 6.38, 6.43; 606/103, 108, 213

(56) References Cited

U.S. PATENT DOCUMENTS

| 4,573,998 A | 3/1986 | Mazzocco |
| 4,681,102 A | 7/1987 | Bartell |
| 4,715,373 A | 12/1987 | Mazzocco et al. |
| 4,763,650 A | 8/1988 | Hauser |
| 4,765,329 A | 8/1988 | Cumming |
| 4,834,094 A | 5/1989 | Patton et al. |
| 4,862,885 A | 9/1989 | Cumming |
| 4,934,363 A | 6/1990 | Smith |
| 4,976,716 A | 12/1990 | Cumming |
| 5,290,310 A | * 3/1994 | Makower et al. ............ 606/213 |
| 5,304,182 A | * 4/1994 | Rheinish et al. ............ 606/107 |
| 5,425,734 A | * 6/1995 | Blake ......................... 606/107 |
| 5,944,725 A | * 8/1999 | Cicenas et al. ............. 606/107 |

FOREIGN PATENT DOCUMENTS

JP        5-103808        4/1993

* cited by examiner

Primary Examiner—Glenn K. Dawson
(74) Attorney, Agent, or Firm—Boniard I. Brown

(57) ABSTRACT

A foldable intraocular lens is stored in its normal unfolded configuration within a lens storage chamber in a lens insertion instrument. The instrument includes a ram which is movable inwardly through the chamber to move the lens into and fold the lens to a compact folded configuration within a bore extending through a tubular portion of the instrument terminating in a slender tip for insertion into a patient's eye through a corneal incision in the eye and through which the folded lens is ejected into the eye by a plunger movable through the bore. An ophthalmic lens insertion kit and lens insertion package including the lens insertion instrument is disclosed.

24 Claims, 3 Drawing Sheets

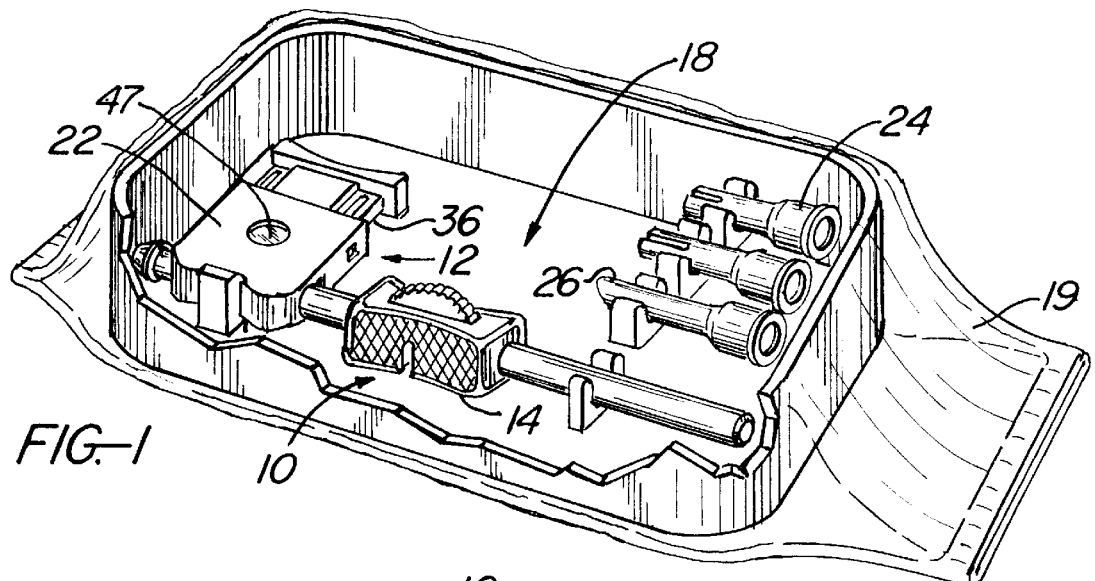
FIG.-1
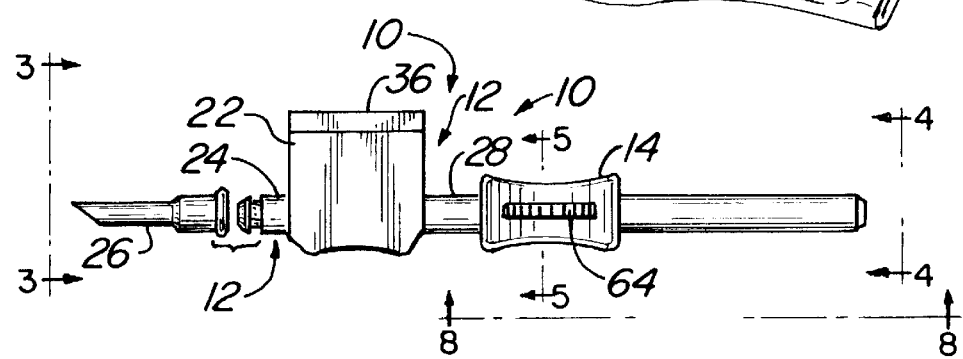
FIG.-2
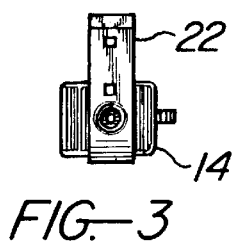
FIG.-3
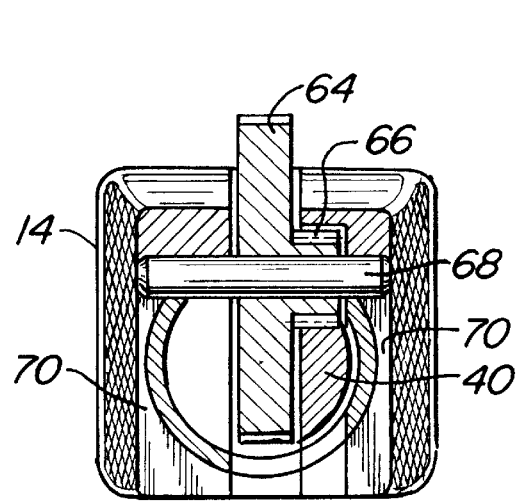
FIG.-5
FIG.-4

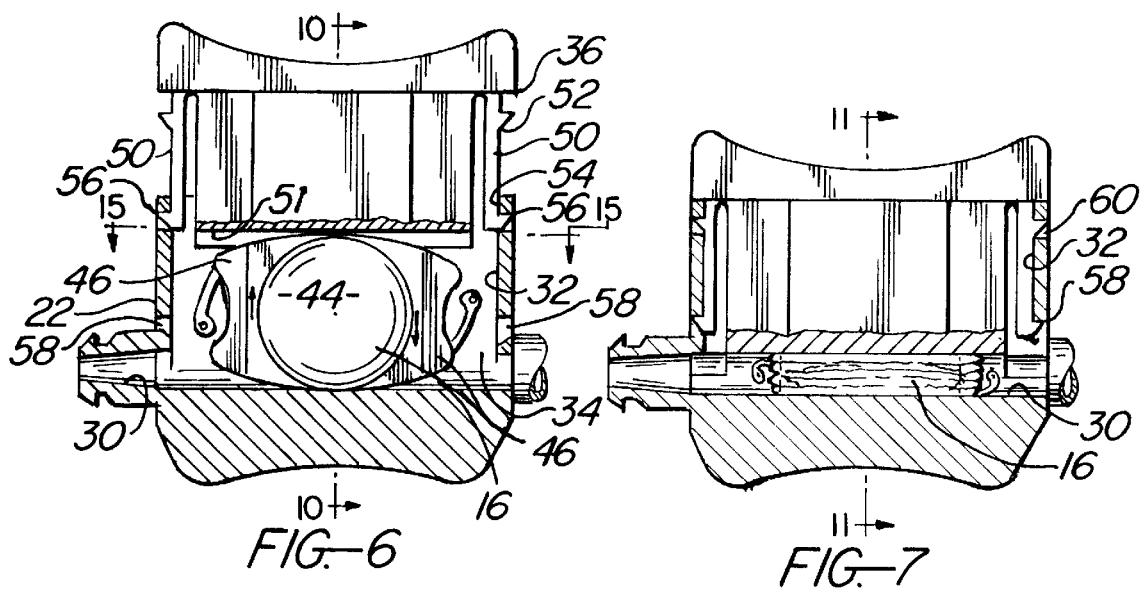
FIG.-6
FIG.-7
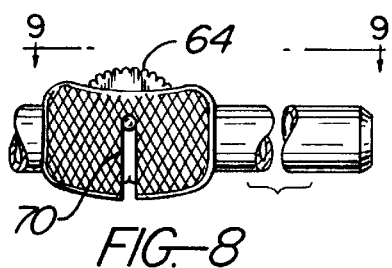
FIG.-8
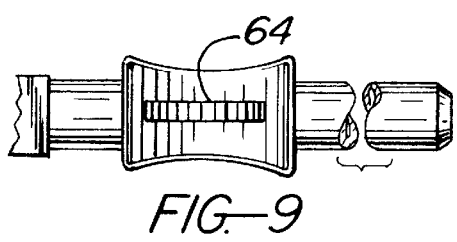
FIG.-9
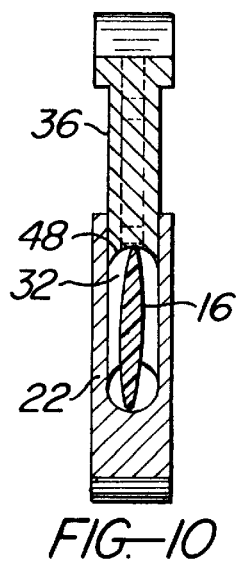
FIG.-10
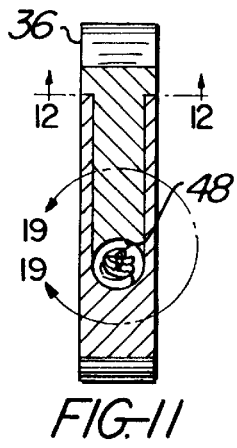
FIG.-11
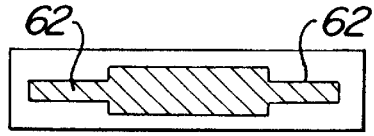
FIG.-12
FIG.-13
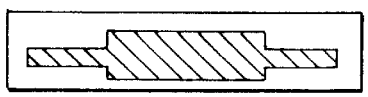
FIG.-14

OPHTHALMIC LENS INSERTION INSTRUMENT AND PACKAGE

RELATED APPLICATION

Reference is made to my copending application Serial No. 08/213,235 filed Mar. 14, 1994.

BACKGROUND OF THE INVENTION

1. Field of the Invention:

This invention relates generally to ophthalmic instruments and more particularly to a novel ophthalmic lens insertion instrument and to an ophthalmic lens insertion kit and lens insertion package embodying the instrument for use in implanting a foldable intraocular lens in a patient's eye.

2. Discussion of the Prior Art:

The human eye is subject to a variety of abnormal conditions that degrade or totally destroy proper optical functioning of the eye. One of the more common of these conditions is a cataract which clouds the natural crystalline lens and obstructs or blocks passage of light rays through the lens to the retina. The ophthalmic procedure for curing a cataract involves extraction of the cataractous natural lens matrix through an incision in the cornea of the eye and implantation of an artificial intraocular lens in the eye through the incision.

In the early days of cataract surgery, the entire cataractous natural lens was removed by a surgical procedure known as intra-capsular lens extraction. While this procedure is occasionally used today in certain circumstances, it has many disadvantages, among the more serious of which is the need to make a relatively large incision in the eye to permit removal of the natural lens through the incision the risks associated with such a large incision.

These disadvantages of intra-capsular lens extraction led to the development in the 1970's of an improved procedure for removing a cataractous natural lens. This improved procedure, known as extra-capsular extraction, involves removal of a central portion or all of the anterior capsule of the natural lens, phacoemulsification of the cataractous natural lens matrix, and aspiration of the emulsified matrix through the resulting anterior capsule opening and a corneal incision. Such extra-capsular extraction with phacoemulsification requires only a relatively small corneal incision on the order of 3 mm in length and thereby greatly reduces or eliminates many of the risks associated with intra-capsular lens extraction.

It was not until the development of the foldable intraocular lens in 1986, however, that this small incision advantage of extra-capsular lens extraction with phacoemulsification could be utilized. This was due to the fact that up until 1986, the only available intraocular lenses were hard lenses which required corneal incisions on the order of 6–8 mm in length for lens insertion. Accordingly, even though the natural lens could be extracted through a 3 mm corneal incision, insertion of a hard intraocular lens into the eye through the incision necessitated enlargement of the incision to 6–8 mm. A foldable intraocular lens, on the other hand, is foldable to a compact folded configuration in which the folded lens is capable of insertion through a 3 mm corneal incision. Accordingly, the development of the foldable intraocular lens enabled extra-capsular extraction of a cataractous natural lens from and implantation of an artificial intraocular lens in a patient's eye through a 3 mm corneal incision in the eye.

A foldable intraocular lens has a normal unfolded lens configuration in which the lens is conditioned to perform its optical lens function in the eye. The lens is foldable to a compact folded configuration for insertion into the eye through a small corneal incision, such as the 3 mm incision required by extra capsular lens extraction with phacoemulsification. In its folded configuration, the lens stores elastic strain energy which unfolds the lens to its normal lens configuration when released within the eye.

A variety of foldable intraocular lenses and instruments for inserting such lenses into the eye have been developed. Among the patents disclosing such lenses and instruments are the following:

U.S. Pat. No. 4,573,998 dated Mar. 4, 1986, to Mazzocco; U.S. Pat. No. 4,681,102 dated Jul. 21, 1987, to Bartell; U.S. Pat. No. 4,715,373 dated Dec. 29, 1987, to Mazzocco et al; U.S. Pat. No. 4,763,650 dated Aug. 16, 1988, to Hauser; U.S. Pat. No. 4,765,329 dated Aug. 23, 1988, to Cumming; U.S. Pat. No. 4,834,094 dated May 30, 1989, to Patton et al; U.S. Pat. No. 4,862,885 dated Sep. 5, 1989, to Cumming; U.S. Pat. No. 4,934,363 dated Jun. 19, 1990, to Smith; U.S. Pat. No. 4,976,716 dated Dec. 11, 1990, to Cumming; Japanese U.S. Pat. No. 5-103,808 dated Apr. 27, 1993, to Kikuchi.

Another lens insertion device for inserting a foldable intraocular lens into a patient's eye is currently being marketed by a company named IOVISION. This IOVISION instrument comprises a lens holder and a ram permanently joined by a flexible strap. The lens holder includes tubular portion having a slender front tip for insertion into a patient's eye, a bore extending axially through the tubular portion and containing a plunger movable through the bore, and a lateral lens storage chamber having an inner end opening laterally to the bore and an open outer end. The chamber is disposed in a plane parallel to and laterally offset from the longitudinal axis of the bore and opens at its inner end laterally into the bore through a wall opening in the bore whose width circumferentially of the bore approximates one quarter the bore circumference. The ram has a laterally facing concave inner end face of approximately this same quarter circumferential width and the same radius of curvature as the bore.

In use, the IOVISION instrument and unfolded lens are stored separately in a sterile condition until needed and are transported separately to the operating room. Within the operating room, the unfolded lens and ram are inserted, lens first, into the lens storage chamber of the instrument through the open outer end of its chamber. The ram is then pressed inwardly through the chamber to force the lens into the bore within the instrument tubular portion. The arcuate inner end face of the ram coacts with the curved wall of the bore to fold or curl the lens to its folded configuration within the bore. The slender tip of the tubular portion is then inserted into the patient's eye through a corneal incision in the eye after which the instrument plunger is moved forwardly through the tubular portion to eject the folded lens from the tubular portion into the eye. The folded lens stores elastic strain energy which unfolds the lens within the eye.

BRIEF DESCRIPTION OF THE INVENTION

The invention provides an improved ophthalmic lens insertion instrument for inserting a foldable intraocular lens in its compact folded configuration into a patient's eye. The invention also provides an ophthalmic lens insertion kit and lens insertion package each including both the improved instrument and a foldable intraocular lens stored in a sterile condition in its normal unfolded configuration with the instrument in total readiness for insertion of the lens into a patient's eye.

The improved ophthalmic instrument of this invention includes a lens insertion assembly and a lens insertion actuator. The lens insertion assembly includes a housing having an elongate tubular portion and a lens storage chamber extending laterally of the tubular portion for storing a foldable intraocular lens in its normal unfolded configuration. The tubular portion contains an axial bore and has a slender front tip for insertion into a patient's eye. The lens storage chamber has an inner end opening laterally into the bore through an opening in the wall of the bore and normally contains lens transfer and folding means for moving the lens into and folding the lens to its compact folded configuration within the bore. The bore contains lens insertion means for ejecting the folded lens from the bore into the patient's eye.

In the preferred embodiments of the invention, the lens transfer and folding means comprises a ram movable between an outer retracted position at the outer end of the lens storage chamber and an inner extended position at the inner end of the chamber. In its outward retracted position, the ram forms with the chamber a lens storage space within the inner end of the chamber. In the inner extended position of the ram, its inner end extends into the wall opening of the bore with the inner end face of the ram substantially flush with and conforming to the curvature of the surrounding wall of the bore. The lens insertion means comprises a plunger movable through the housing bore, and an end extending rearwardly from the tubular portion. The insertion actuator of the instrument is mounted on the tubular portion and is operable to move the plunger of the insertion assembly forwardly through the bore in the tubular portion.

The lens insertion assembly is designed to store for a prolonged period of time a foldable intraocular lens in its normal unfolded configuration in a storage position within the lens storage space of the lens storage chamber with the assembly ram located in its outwards retracted position in the chamber. Inward movement of the ram to its inward extended position in the chamber pushes the unfolded lens inwardly into the bore of the housing tubular portion and then curls or folds the lens to its folded configuration within the bore with the folded lens situated in a pre-insertion position within the bore. The assembly plunger is then moved forwardly through the bore to eject the folded lens from the insertion assembly through the tip of its tubular portion.

A feature of the presently preferred inventive embodiments resides in the fact that the lens storage chamber and ram of the insertion assembly have a common longitudinal medial plane containing the longitudinal axis of the tubular portion bore so that the bore is laterally centered relative to the chamber and ram. The wall opening between the bore and chamber and the inner end face of the ram are bisected circumferentially by this medial plane and have circumferential widths approximating one-half the circumference of the bore. This feature assures optimum folding or curling of the lens to its folded configuration by inward movement of the ram.

A unique and important advantage of the present lens insertion instrument resides in its ability to store the lens for a prolonged period of time in its normal unfolded configuration directly within the lens insertion assembly with the ram positioned in its outwards retracted position in the lens storage chamber. The lens is thus stored in total readiness for insertion of the lens into a patient's eye without the necessity of inserting the lens and ram into the chamber in the operating room as required in the IOVISION instrument described earlier. The insertion assembly and its stored unfolded lens together form a lens insertion kit which can be stored in a sterile condition, with or without the insertion actuator, as desired, depending on whether the actuator is permanently attached to or removable from the assembly. According to a feature of the invention, this lens insertion kit can be removably housed in an instrument holder contained within a sealed sterile pouch. The pouch, holder, and lens insertion kit together form a sterile lens insertion package which can be stored until needed. The instrument holder includes loading means for operating the insertion assembly ram to move the lens into and fold the lens within the bore of the assembly housing prior to removal of the assembly from the holder.

BRIEF DESCRIPTION OF THE DRAWINGS

FIG. 1 is a perspective view of a preferred ophthalmic lens insertion package according to the invention, including a lens insertion kit mounted in a holder and enclosed in a sterile pouch;

FIG. 2 is a top view of the lens insertion assembly of the lens insertion kit of FIG. 1;

FIG. 3 is a view taken at line 3—3 in FIG. 2;

FIG. 4 is a view taken at line 4—4 in FIG. 2;

FIG. 5 is an enlarged sectional view taken at line 5—5 in FIG. 2;

FIGS. 6 and 7 are sectional views of ram and receptacle components utilized with the present invention, showing the operation thereof in the folding of an intraocular lens;

FIG. 8 is an enlarged fragmentary view, taken at line 8—8 in FIG. 2;

FIG. 9 is a view taken at line 9—9 in FIG. 8;

FIG. 10 is a sectional view taken at line 10—10 in FIG. 6;

FIG. 11 is a sectional view taken at line 11—11 in FIG. 7;

FIGS. 12–14 are sectional views taken at line 12—12 in FIG. 11, and showing cross-sectional configurations of a ram utilized with the invention;

DESCRIPTION OF A PREFERRED EMBODIMENT OF THE INVENTION

Figure 15:
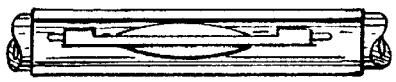
FIG. 15 is a sectional view taken at line 15—15 in FIG. 6.
Figure 16:
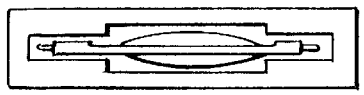
FIGS. 16–18 are views taken at line 16—16 in FIG. 25, showing different receptacle slot configurations utilized with the invention.
Figure 17:
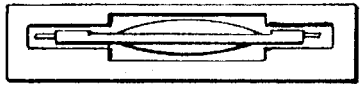

Referring to the drawings, there is illustrated an insertion instrument 10 (FIG. 2) according to the invention for inserting an intraocular lens into a patient's eye via an incision in the cornea. The instrument 10 includes a lens insertion assembly 12 and an insertion actuator 14.

As described further herein, lens insertion assembly 12 is adapted to receive a foldable intraocular lens 16 in unfolded configuration. The lens insertion assembly with the unfolded lens forms a lens insertion kit 18 according to the invention for storing the unfolded lens in a sterile condition in readiness for insertion into a patient's eye. Preferably, according to the invention, the sterilized lens insertion kit 18 is sealed and releasably held in a sterile container or pouch 19 to provide a lens insertion package (FIG. 1) according to the invention for storing the unfolded lens 16 until needed.

Figure 22:
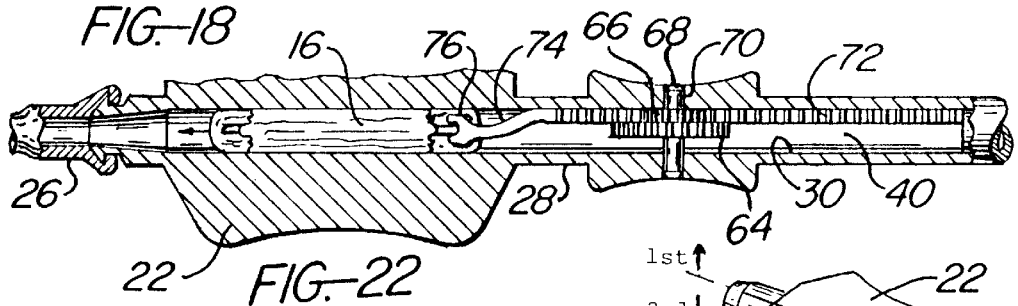
FIG. 22 is an enlarged partial sectional view taken in FIG. 2.

Lens insertion assembly 12 includes a receptacle 22 and an elongate tubular portion 24 with an anterior nozzle or tip 26 for insertion into the patient's eye and an opposite posterior lens portion 28. Extending axially through tubular portion 24 is a bore 30 (FIGS. 6 and 22). The assembly housing includes the receptacle 22 which is preferably formed integrally with and is in alignment of the tubular portion. The receptacle has lens storage chamber 32 extending laterally of the bore 30. The chamber has an inner end opening laterally into the bore 30 through an opening in the wall of the bore between the ends of the bore and an opposite outer end opening through the outer end of a receptacle 22.

The foldable lens illustrated is a plate haptic lens formed of appropriate flexible optical lens material and having a central optic 44 and flat plate hapties 46 (FIGS. 6 and 25) joined to opposite edges of the optic. When unrestrained, the lens assumes its normal unfolded configuration of FIGS. 6 and 25, in which the haptics are disposed in a common plane transverse to the axis of the optic. It will be evident, however, that other types of foldable lenses may be utilized. The unfolded lens is centered endwise between the longitudinal edges of the ram with the lens disposed transversely of the longitudinal edges of the ram (FIG. 6), and with the lens located substantially in the medial plane of the ram.

A lens storage space 34 at the inner end of the chamber receives the foldable intraocular lens 16 in a storage position (FIG. 6) within the storage space with the lens disposed in normal unfolded configuration. A ram 36 serves as lens transfer and folding means and cooperates with the chamber to form the lens storage space 34. The ram is operable by the instrument user to move the unfolded lens from its storage position in the space 38 into the housing bore 30 through its wall opening and to fold the lens to a compact folded configuration with the lens disposed in a pre-insertion position (FIGS. 7 and 11) within the bore. A plunger 40 (FIGS. 5 and 22) serves as a lens insertion means for moving the folded lens forwardly through the bore from its pre-insertion position, and through the tubular portion 24 and the outlet nozzle or tip 26 to eject the lens from the insertion assembly through the tip into the eye of the patient. At least one side wall of the housing chamber 32 contains a small window 47 through which the storage space and lens therein may be viewed.

The ram and receptacle have mating male and female configurations, and respective cross-sectional configurations of the ram correspond to respective configurations of the slot in receptacle 22. The receptacle slot includes a central portion 60 which accommodates the optic of the lens and side or wing portions 62 to receive and support the haptics of the lens, and thus prevent the optic 44 from contacting any surface. The cross-sectional configuration of the slot may have any of the configurations shown in FIGS. 12–14, which are sectional views taken at line 12—12 in FIG. 11.

As shown in FIGS. 25 and 12 to 18, the chamber 32 and ends of the ram have complementary configurations in transverse cross-section, and have a common longitudinal medial plane parallel to the flat sides of the ram.

Referring to FIGS. 10 and 11, the inner end of the ram has an arcuate endface 48 curved about an axis parallel to the medial plane of the ram and transverse to the length of the ram. The outer end of the ram 36 is accessible for application of manual pressure to urge the ram into the receptacle 22. In this position, inner end of the ram is positioned with its ram edges seated against the longitudinal edges of the wall opening, with the arcuate inner end face 51 of the ram flush with the inner wall surface of the bore, and faces the opposing inner wall surface of the bore opposite the wall opening. The ram inner end face is curved like the opposing inner wall surface and cooperates to define a circular section of the bore.

As shown in FIGS. 6 and 7, the ram has longitudinal resilient arms 50 with prongs 52, 56 spaced apart on each of these arms which are on opposite sides of the ram, as shown. Prongs 52, 56 on each arm are engageable respectively with notches 58, 60 defined in opposite sides of the receptacle inner walls (FIGS. 6 and 7), the prongs being spaced apart like the notches for concurrent engagement.

The prongs and notches serve to retain the ram in its retracted storage position when the lens is disposed in the receptacle (FIG. 6) and, upon the user or surgeon manually urging the ram to compress and fold the lens, the prongs and notches serve to retain the ram in the extended closed position of FIG. 7.

Figure 18:
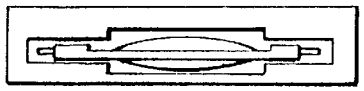
Figure 19:
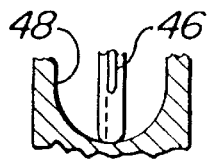
FIGS. 19–21 are fragmentary sectional views taken at encircled portion 19—19 in FIG. 11, showing initiation of lens folding by the respective slot configurations of FIGS. 16–18.
Figure 20:
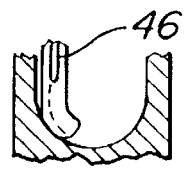
Figure 21:
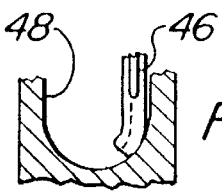
Figure 25:
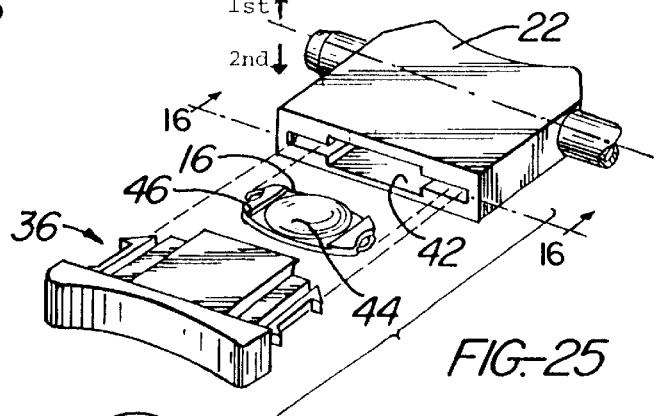
FIG. 25 is an exploded perspective view of a ram and receptacle of the invention in relation to an intraocular lens.
Figure 24A:
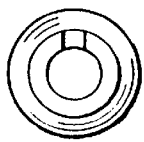
FIGS. 24A–24C are sectional views taken at line 24—24 in FIG. 23, showing outlet tips configurations utilized in injecting a lens into an eye.
Figure 24B:
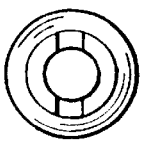
Figure 24C:
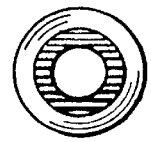

With a slot of the type shown in FIGS. 12 and 25, upon compression of the lens by the ram, the lens engages the curved arcuate receptacle wall in the manner indicated in FIG. 19. With the slot side portions thus disposed centrally in the receptacle, the lens may be folded to open upwardly toward the ram or downwardly away from the ram i.e., in the terms employed in the profession, "taco-up" or "taco-down". With the slot side portions configuration positions of FIGS. 13 and 17, the lens engages the curved surface in the manner indicated in FIG. 20, thus to fold the lens in a downwardly opening away from the ram or "taco-down" configuration. With slot side portions configurated and positioned as shown in FIG. 18, the lens engages the curved surface in the manner indicated in FIG. 21, with the lens being folded in an upwardly opening up configuration toward the ram or "taco-up". Receptacles and rams may be provided the appropriate ram and slot configurations to provide lens folding as desired by the surgeon.

The actuator mechanism 14 is assembled by finger wheel 64 and pinion gear 66 being positioned in the actuator body and the plunger then being inserted into the tubular portion, being noted that the plunger has a portion with the cross-section configuration shown in FIG. 5, which accommodates finger wheel and pinion. The actuator mechanism comprises a receptacle 22 on the tubular portion, and typically formed integrally therewith. A finger wheel 64, pinion gear 66 and axle 68 (FIGS. 5 and 22) are typically integrally formed, as by molding, and are mounted in the body 14 via slot 70 in opposite sides of the body, as shown, and retained as by force-fitting. As shown, the upper portion of the body is preferably contoured to facilitate manual engagement.

As shown (FIG. 22), the plunger 40 has defined thereon teeth 72 to provide a rack to engage the pinion 66 and has an end portion 76 of U-shaped configuration to engage an end portion of the lens.

Figure 23:
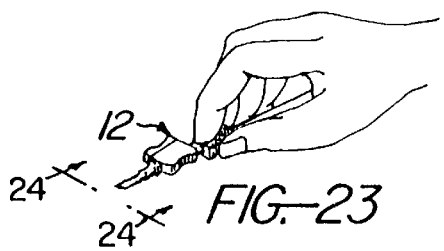
FIG. 23 is a perspective view showing the insertion device of FIG. 2 in the hand of a user during insertion of a lens utilizing a device of the invention.

In operating the actuator mechanism, the surgeon grasps the device between the thumb and second finger (FIG. 23) and rotates finger wheel 64 with the index finger to rotate pinion gear 66 and move the plunger to urge the lens outwardly through the nozzle or tip into the eye of a patient.

Thus there has been shown and described a novel ophthalmic lens insertion instrument and package which fulfills all the objects and advantages sought therefor. Many changes, modifications, variations and other uses and applications of the subject invention will, however, become apparent to those skilled in the art after considering this specification together with the accompanying drawings and claims. All such changes, modifications, variations and other uses and applications which do not depart from the spirit and scope of the invention are deemed to be covered by the invention which is limited only by the claims which follow.

What is claimed is:

1. An ophthalmic instrument for inserting an intraocular lens into a patient's eye through a corneal incision in the eye, said instrument comprising:

a housing including a tubular portion having a relatively slender tip for insertion into the patient's eye, a bore extending axially through said tubular portion, and a lens storage chamber having opposite walls and an inward end opening laterally to said bore and an opposite outer end, a lens having an optic and oppositely extending haptics and a normally unfolded configuration, lens transfer and folding means within said chamber forming with the chamber a lens storage space within the inward end of the chamber for storing the lens in its normal unfolded configuration and operable by an instrument user to move the unfolded lens from said storage space into said bore and fold the lens to a compact folded configuration with the folded lens located in a pre-insertion position within said bore, said lens transfer and folding means comprises a ram movable through said chamber between a normal retracted position within the outer end of the chamber wherein the ram and chamber form said lens storage space and an inward extended position wherein the ram is disposed to retain the folded lens in said pre-insertion position, said ram having an arcuate end face confronting an arcuate inner wall of the tubular portion, said lens being foldable by a rolling action thereon by the ram arcuate face and the confronting arcuate wall of said housing tubular portion into the folded configuration wherein the haptics are folded over each other, said ram and said opposite walls of said storage chamber having interfitting cross-sectional configurations, the ram having laterally extending reduced wing portions and the chamber walls defining mating laterally extending slots to receive the ram wing portions and said lens haptics, whereby contact of the lens optic with chamber walls is prevented, cooperating means on said housing and said ram releasably retaining said ram in at least one of said retracted and extended positions, lens insertion means for moving the folded lens through said bore from said pre-insertion position toward and through said tip of said tubular portion for ejecting the folded lens from said tubular portion through said tip, said lens insertion means including, an insertion actuator connected with said tubular portion and engaging a plunger for operation by the instrument user to move the plunger forwardly through said bore.

2. An ophthalmic instrument for inserting into a patient's eye through a corneal incision in the eye a foldable intraocular lens having an optic and oppositely extending plate haptics, the lens having a normal unfolded configuration and being foldable to a compact folded configuration, said instrument comprising:

a housing including a tubular portion having a relatively slender tip for insertion into the patient's eye, a bore extending axially through said tubular portion, a lens storage chamber having an inner end opening laterally to said bore through a wall opening in the wall of said bore and an opposite outer end, and said bore having a wall surface opposite and facing said wall opening, a ram movable through said chamber between an outward retracted position in the outer end of said chamber and an inward extended position and having an inner end which enters said wall opening in said extended position and an inner end face at said inner end which faces said wall surface of said bore, said ram and opposing walls of said storage chamber having interfitting cross-sectional configurations, the ram having laterally extending reduced wing portions and the chamber walls defining mating laterally extending slots to receive the ram wing portions and said lens haptics, whereby contact of the lens optic with slots outer ends and chamber walls is prevented, coacting means on the ram and a receptacle portion of the housing for releasably retaining the ram in at least one of said inward extended position and said outward retracted position wherein the ram and chamber define said lens storage chamber, a plunger movable through said bore, and wherein said ram is movable inwardly through said chamber by an instrument user to move the unfolded lens from said chamber into said bore and fold the lens to its compact folded configuration with the folded lens disposed in a pre-insertion position within said bore, an end face of said ram being cylindrically curved about an axis parallel to the bore axis to substantially the same radius as said bore to roll said lens when said ram occupies its inward extended position, and said plunger is movable through said bore to eject the folded lens from said pre-insertion position through said tip of said tubular portion.

3. An ophthalmic instrument according to claim 1, wherein:

said coacting means on the ram comprise prongs on resilient fingers at each side of the ram, and the coacting means on the receptacle comprises notches in receptacle inner walls and engageable with the prongs to retain the ram in position, the prongs being disengaged from the notches upon application of moving force on the ram.

4. An ophthalmic instrument according to claim 2, wherein:

the receptacle portion of the housing defines said slots to extend in first and second directions transversely to a receptacle bore axis, side slot portions being offset in the first direction transversely of the axis of the bore for coaction with the ram and an arcuate surface of the bore to effect folding of outer portions of the lens in the second direction transversely of the bore axis.

5. An ophthalmic instrument for inserting into a patient's eye through a corneal incision in the eye a foldable intraocular lens having an optic and oppositely extending haptics, the lens having a normal unfolded configuration and being foldable to a compact folded configuration, said instrument comprising:

a housing including a tubular portion having a relatively slender tip for insertion into the patient's eye, a bore extending axially through said tubular portion, a lens storage chamber having an inner end opening laterally to said bore through a wall opening in the wall of said bore and an opposite outer end, and said bore having a wall surface opposite and facing said wall opening, a ram movable through said chamber between an outward retracted position in the outer end of said chamber and an inward extended position and having an inner end which enters said wall opening in said extended position and an inner end face at said inner end which faces said wall surface of said bore, said ram and opposing walls of said storage chamber having interfitting cross-sectional configurations, the ram having laterally extending reduced wing portions and the chamber walls defining mating laterally extending slots to receive the ram wing portions and said lens haptics, whereby contact of the lens optic with chamber walls is prevented, the slots being generally centered in the housing and wherein the ram and the receptacle have a common medial plane extending therethrough and intersecting the longitudinal axis of the tube passage, coacting means on the ram and a receptacle portion of the housing for releasably retaining the ram in at least one of said inward extended position and said outward retracted position wherein the ram and chamber define said lens storage chamber, a plunger movable through said bore, and wherein
said ram is movable inwardly through said chamber by an instrument user to move the unfolded lens from said chamber into said bore and fold the lens to its compact folded configuration with the folded lens disposed in a pre-insertion position within said bore, and
said plunger is movable through said bore to eject the folded lens from said pre-insertion position through said tip of said tubular portion.

6. An instrument according to claim 5 wherein:
the end face of said ram is cylindrically curved about an axis parallel to the bore axis to substantially the same radius as said bore to roll said lens when said ram occupies its inward extended position.

7. An ophthalmic instrument for inserting into a patient's eye through a corneal incision in the eye a foldable intraocular lens which has a normal unfolded configuration and is foldable to a compact folded configuration, said instrument comprising:
a housing including a tubular portion having a relatively slender tip for insertion into the patient's eye, a bore extending axially through said tubular portion, a lens storage chamber having an inner end opening laterally to said bore through a wall opening in the wall of said bore whose width circumferentially of the bore approximates at least one half of the bore circumference, and said bore having a concave wall surface opposite and facing said wall opening and having a width circumferentially of the bore approximating one half the circumference of the bore,
a ram movable through said chamber between an outward retracted position in an outer end of said chamber and an inward extended position and having an inner end which enters said wall opening in said inner extended position and a concave inner end face at said inner end having a circumferential width circumferentially of said bore approximating one half the circumference of said bore, said chamber and ram having a common longitudinal medial plane containing the longitudinal axis of said bore and substantially circumferentially bisecting said wall opening, said wall surface, and said ram inner end face, a plunger movable through said bore, and wherein
said chamber can receive said lens in its unfolded configuration and in a position between said inner end face of said plunger and said wall surface of said bore when said ram occupies its outer retracted position in said chamber,
said ram is movable inwardly through said chamber by an instrument user to move the unfolded lens from said chamber into said bore and fold the lens to its compact folded configuration with the folded lens disposed in a pre-insertion position within said bore, and
said plunger is movable through said bore to eject the folded lens from said pre-insertion position through said tip of said tubular portion.

8. An ophthalmic instrument according to claim 7, wherein:
said wall surface of said bore is cylindrically curved about the axis of said bore, and said end face of said ram is cylindrically curved about an axis parallel to said bore axis.

9. An ophthalmic instrument according to claim 7, wherein:
said wall surface of said bore and said ram end face are cylindrically curved to substantially the same radius and form a cylindrical portion of said bore when said ram occupies its inward extended position.

10. An ophthalmic instrument according to claim 7, including:
a window in said housing opposite said lens storage chamber which the lens may be viewed.

11. An ophthalmic instrument for inserting an intraocular lens into a patient's eye through a corneal incision in the eye, said instrument comprising:
a lens insertion assembly comprising a housing including a tubular portion having a relatively slender front tip for insertion into the patient's eye and an opposite rear end, a bore extending axially through said tubular portion, and a lens storage chamber having walls for storing said lens in a normal unfolded configuration and having an inner end opening laterally to said bore,
a lens having an optic and oppositely extending plate haptics and a normally unfolded configuration,
a ram operable by an instrument user to move the unfolded lens to a compact folded configuration with the folded lens located in a pre-insertion position within said bore,
said ram having an arcuate end face confronting an arcuate wall of the tubular portion,
said lens being foldable by a rolling action thereon by the ram arcuate face and a confronting arcuate wall of said housing tubular portion into the folded configuration wherein the haptics are folded over each other,
a plunger movable forwardly through said bore for moving the folded lens through said bore from said pre-insertion position toward and through said tip of said tubular portion for ejecting the folded lens from said tubular portion through said tip,
said ram and said chamber walls having interfitting cross-sectional configurations, the ram having laterally extending reduced wing portions and the chamber walls having mating laterally extending slot portions to receive the lens haptics, whereby contact of the lens optic with chamber walls is prevented, and insertion actuator means on the tubular portion and manually operable to engage cooperating means on the plunger for manual operation to move the plunger forwardly through said bore.

12. An ophthalmic instrument according to claim 11, wherein:

the insertion actuator means comprises a pinion rotatable by the instrument user to cooperate with rack teeth on the plunger.

13. An ophthalmic instrument according to claim 11, wherein:

said insertion actuator means is permanently joined to said housing tubular portion.

14. An ophthalmic instrument for inserting into a patient's eye through a corneal incision in the eye a foldable intraocular lens having oppositely extending haptics and a normal unfolded configuration and being foldable to a compact folded configuration, said instrument comprising:

a housing including a tubular portion having a relatively slender front tip for insertion into the patient's eye and an opposite rear end, a bore extending axially through said tubular portion, and a lateral housing portion projecting laterally from said tubular portion between said ends of the tubular portion containing a chamber having an inner end opening laterally to said bore through a wall opening in the bore and an opposite open outer end, a ram having inner and outer ends movable inwardly through said chamber from a normal outward retracted position in which said inner end of the ram is spaced outwardly from the inner chamber end to define a lens storage space within an inner end portion of the chamber to an inner extended position in which the inner end of the ram extends through said wall opening, said ram and said housing having interfitting cross-sectional configurations, the ram having laterally extending reduced wing portions and the housing having mating laterally extending slot portions to receive the lens haptics, whereby contact of the lens optic with chamber walls is prevented, coacting means on said ram and housing for releasably retaining said ram in its outward retracted position to define the lens storage space, a plunger having front and rear ends and movable longitudinally in said bore between a rear retracted position wherein said front end of the Plunger is located rearwardly of said wall opening and a forward extended position wherein said front end of the plunger extends through said front tip of said tubular housing portion, and wherein said ram having an arcuate end face opposing an arcuate inner wall surface of said housing tubular portion, said ram being movable from its outward retracted position to its inner extended position by an instrument user to move the unfolded lens from a storage position through said wall opening into said bore and then fold the lens by rolling action between the ram arcuate face and a confronting arcuate inner wall of the housing tubular portion into its compact folded configuration with the lens situated in a pre-insertion position within said bore while said plunger occupies its rear retracted position in said bore, said plunger is movable forwardly through said bore for moving the folded lens through said bore from said pre-insertion position toward and then through said tip of said tubular housing portion, an insertion actuator engaging a plunger for operation by a user of a pinion to move the plunger forwardly through said bore.

15. An ophthalmic instrument according to claim 14, wherein:

said coacting means on the ram comprise prongs on resilient fingers at each side of the ram, and the coacting means on the housing comprises notches in receptacle inner walls and engageable with the prongs to retain the ram in position, the prongs being disengaged from the notches upon application of moving force on the ram.

16. An ophthalmic instrument according to claim 14, wherein:

said opposing inner wall surface of said bore is cylindrically curved with a certain radius about the axis of said bore, and said end face of said ram is cylindrically curved with said certain radius about an axis parallel to the axis of said bore, and said chamber and ram have a common longitudinal medial plane which contains the longitudinal axis of said bore and substantially circumferentially bisects said wall opening, said inner wall surface, and said ram inner end face.

17. An ophthalmic instrument according to claim 16, wherein:

said coacting means on the ram comprise prongs on resilient fingers at each side of the ram, and the coacting means on the housing comprises notches in receptacle inner walls and engageable with the prongs to retain the ram in position, the prongs being disengaged from the notches upon application of moving force on the ram.

18. An ophthalmic instrument according to claim 14, wherein:

the housing slot portions extend in first and second directions transversely of the axis of the bore and are offset in the second direction transversely of the axis of the bore for coaction with the ram and an arcuate surface of the bore to effect folding of outer portions of the lens in the first direction transversely of the bore axis.

19. An ophthalmic instrument for inserting into a patient's eye through a corneal incision in the eye a foldable intraocular lens having oppositely extending haptics and a normal unfolded configuration and being foldable to a compact folded configuration, said instrument comprising:

a housing including a tubular portion having a relatively slender front tip for insertion into the patient's eye and an opposite rear end, a bore extending axially through said tubular portion, and a lateral housing portion projecting laterally from said tubular portion between said ends of the tubular portion containing a chamber having an inner end opening laterally to said bore through a wall opening in the bore and an opposite open outer end, a ram having inner and outer ends movable inwardly through said chamber from a normal outward retracted position in which said inner end of the ram is spaced outwardly from the inner chamber end to define a lens storage space within an inner end portion of the chamber to an inner extended position in which the inner end of the ram extends through said wall opening, an inner wall surface of said tubular portion bore being cylindrical curved with a certain radius about the axis of said bore, and an end face of said ram is cylindrically curved with said certain radius about an axis parallel to the axis of said bore, said chamber and ram having a common longitudinal medial plane which contains the longitudinal axis of said bore and substantially circumferentially bisects said wall opening, said inner wall surface, and said ram inner end face, and wherein the ram and the housing have interfitting cross-sectional configurations, the ram having laterally extending reduced wing portions and the housing having mating laterally extending slot portions to receive the lens haptics, whereby contact of the lens optic with slot walls is prevented, coacting means on said ram and housing for releasably retaining said ram in its outwardly spaced position to define the lens storage space, a plunger having front and rear ends and movable longitudinally in said bore between a rear retracted position wherein said front end of the plunger is located rearwardly of said wall opening and a forward extended position wherein said front end of the plunger extends through said front tip of said tubular housing portion, and wherein said ram is movable from its outward retracted position to its inner extended position by an instrument user to move the unfolded lens from said storage position through said wall opening into said bore and then fold the lens to its compact folded configuration with the lens situated in a pre-insertion position within said bore while said plunger occupies its rear retracted position in said bore, said plunger is movable forwardly through said bore for moving the folded lens through said bore from said pre-insertion position toward and then through said tip of said tubular housing portion, and the end face of said ram faces an opposing wall surface of said bore opposite said wall opening when said ram occupies its inner extended position.

20. An ophthalmic lens insertion kit comprising:

a housing including a tubular portion having a relatively slender tip for insertion into the patient's eye, a bore extending axially through said tubular portion, a lens storage chamber having an inner end opening laterally to said bore through a wall opening in the wall of said bore whose width circumferentially of the bore approximates at least one half of the bore circumference, and said bore having a concave inner wall surface opposite and facing said wall opening and having a width circumferentially of the bore approximating one half the circumference of the bore, a ram in said chamber in an outward retracted position in the outer end of said chamber wherein the ram forms with the chamber a lens storage space within the inner end of the chamber, and said ram being movable inwardly through the chamber to an inward extended position and having an inner end which enters said wall opening in said inner extended position and a concave inner end face at said inner end having a width circumferentially of said bore approximating one half the circumference of said bore, said chamber and ram having a common longitudinal medial plane containing the longitudinal axis of said bore and substantially circumferentially bisecting said wall opening, concave inner wall surface, and said ram inner end face, a foldable intraocular lens positioned in said lens storage space in its normal unfolded configuration, a plunger movable through said bore, and wherein said ram is movable inwardly through said chamber to its inward extended position by an instrument user to move the unfolded lens from said storage space into said bore and fold the lens to a compact folded configuration with the folded lens disposed in a pre-insertion position within said bore, and said plunger is movable through said bore to eject the folded lens from said pre-insertion position through said tip of said tubular portion.

21. A lens insertion kit according to claim 20, wherein:

said concave inner wall surface of said bore is cylindrically curved about the axis of said bore, and said end face of said ram is cylindrically curved about an axis parallel to said bore axis.

22. An ophthalmic lens insertion instrument comprising:

a lens insertion kit comprising a housing including a tubular portion having a relatively slender front tip for insertion into the patient's eye and an opposite rear end, a bore having a longitudinal axis extending through said tubular portion, and a chamber having an inner end opening laterally to said bore, a ram for lens transfer and folding disposed within said chamber and forming with the chamber a lens storage space within the inner end of the chamber, a foldable intraocular lens having a normal unfolded configuration situated in a storage position within said storage space with the lens in its normal unfolded configuration, the ram and the chamber having a common medial plane extending therethrough and intersecting the longitudinal axis of the bore said ram being operable by an instrument user to move the unfolded lens from said chamber into said bore and fold the lens to its compact folded configuration with the folded lens located in a pre-insertion position within said bore, and a plunger movable forwardly through said bore for moving the folded lens through said bore from said pre-insertion position toward and through said tip of said tubular portion for ejecting the folded lens from said tubular portion through said tip, and an insertion actuator connected with said tubular portion and engaging the plunger for operation by the instrument user to move the plunger forwardly through said bore.

23. An ophthalmic instrument according to claim 22, wherein:

the insertion actuator comprises a pinion rotatable by the instrument user to cooperate with rack teeth on the plunger.

24. An ophthalmic instrument according to claim 22, wherein:

said insertion actuator is permanently joined to said housing tubular portion.

* * * * *